United States Patent
Loccufier et al.

(10) Patent No.: US 11,407,913 B2
(45) Date of Patent: Aug. 9, 2022

(54) INKJET INKS FOR MANUFACTURING PRINTED CIRCUIT BOARDS

(71) Applicant: Agfa-Gevaert NV, Mortsel (BE)

(72) Inventors: Johan Loccufier, Mortsel (BE); Rita Torfs, Mortsel (BE)

(73) Assignee: AGFA-GEVAERT NV, Mortsel (BE)

( * ) Notice: Subject to any disclaimer, the term of this patent is extended or adjusted under 35 U.S.C. 154(b) by 35 days.

(21) Appl. No.: 16/977,540

(22) PCT Filed: Feb. 26, 2019

(86) PCT No.: PCT/EP2019/054676
§ 371 (c)(1),
(2) Date: Sep. 2, 2020

(87) PCT Pub. No.: WO2019/166405
PCT Pub. Date: Sep. 6, 2019

(65) Prior Publication Data
US 2021/0002500 A1  Jan. 7, 2021

(30) Foreign Application Priority Data
Mar. 2, 2018 (EP) .................................. 18159698

(51) Int. Cl.
| | | |
|---|---|---|
| C09D 11/38 | (2014.01) | |
| B41M 5/00 | (2006.01) | |
| C07C 323/12 | (2006.01) | |
| C09D 11/101 | (2014.01) | |
| H05K 3/28 | (2006.01) | |

(52) U.S. Cl.
CPC ........... C09D 11/38 (2013.01); B41M 5/0023 (2013.01); C07C 323/12 (2013.01); C09D 11/101 (2013.01); H05K 3/28 (2013.01); H05K 2203/0548 (2013.01)

(58) Field of Classification Search
CPC .......... C09D 11/101; C09D 11/30; B41J 2/01; B41M 5/0058; H05K 3/0076; H05K 3/28
See application file for complete search history.

(56) References Cited

U.S. PATENT DOCUMENTS

| | | | | |
|---|---|---|---|---|
| 3,657,197 A * | 4/1972 | Freyermuth | ............... | C08F 8/14 528/377 |
| 3,725,064 A * | 4/1973 | Field | ............... | C08F 8/14 430/281.1 |
| 4,636,534 A * | 1/1987 | Nawata | ............... | G03F 7/027 522/116 |
| 2006/0166137 A1 * | 7/2006 | Mitsumoto | ............... | B41N 1/08 430/270.1 |
| 2007/0068898 A1 * | 3/2007 | Lorenz | ............... | B41J 2/01 216/27 |
| 2009/0136678 A1 | 5/2009 | Nakamura et al. | | |
| 2012/0207943 A1 * | 8/2012 | Enomoto | ............... | B82Y 10/00 427/517 |
| 2014/0227493 A1 | 8/2014 | Enomoto | | |
| 2017/0218520 A1 * | 8/2017 | De Mondt | ............... | C23F 1/16 |
| 2020/0094542 A1 * | 3/2020 | Hirano | ............... | C08F 2/44 |

FOREIGN PATENT DOCUMENTS

| | | |
|---|---|---|
| DE | 10063332 A1 | 6/2002 |
| EP | 2065448 A1 | 6/2009 |
| EP | 2302010 A1 | 3/2011 |
| EP | 3000853 A1 | 3/2016 |
| EP | 3321331 A1 | 5/2018 |
| EP | 3321332 A1 | 5/2018 |
| JP | 2003-105272 A | 4/2003 |

(Continued)

OTHER PUBLICATIONS

Office Action dated Jan. 20, 2021 relating to Indian Patent Application No. 202017036510, 6 pages.

(Continued)

*Primary Examiner* — John Zimmermann
(74) *Attorney, Agent, or Firm* — Leydig, Voit & Mayer, Ltd.

(57) ABSTRACT

A method of manufacturing a Printed Circuit Board (PCB) wherein an inkjet printing step is used, characterized in that in the inkjet printing step a radiation curable inkjet ink comprising an adhesion promoter having a chemical structure according to Formula I is jetted and cured on a substrate, wherein X is selected from the group consisting of O and $NR_3$, $L_1$ and $L_2$ independently represent a divalent linking group comprising from 2 to 20 carbon atoms, $R_1$ is selected from the group consisting of hydrogen, a substituted or unsubstituted alkyl group and a substituted or unsubstituted aryl group, $R_2$ is selected from the group consisting of a substituted or unsubstituted alkyl group, a substituted or unsubstituted alkenyl group, a substituted or unsubstituted alkynyl group, a substituted or unsubstituted alkaryl group, a substituted or unsubstituted aralkyl group and a substituted or unsubstituted (hetero)aryl group, R3 is selected from the group consisting of hydrogen, a substituted or unsubstituted alkyl group, a substituted or unsubstituted alkenyl group, a substituted or unsubstituted alkynyl group, a substituted or unsubstituted alkaryl group, a substituted or unsubstituted aralkyl group and a substituted or unsubstituted (hetero)aryl group, n represents an integer from 0 to 4, any of $L_1$, $L_2$ and $R_2$ may represent the necessary atoms to form a 5 to 8 membered ring.

I

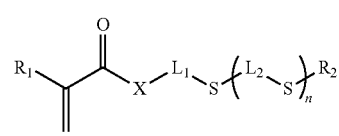

13 Claims, No Drawings

(56) References Cited

FOREIGN PATENT DOCUMENTS

| | | |
|---|---|---|
| JP | 2005-539391 A1 | 12/2005 |
| JP | 2006160824 A | 6/2006 |
| JP | 2009-127030 A1 | 6/2009 |
| JP | 2010006977 A | 1/2010 |
| KR | 1020050057461 A | 6/2005 |
| WO | 2004/026977 A1 | 4/2004 |
| WO | WO 2004/026977 A1 | 4/2004 |
| WO | WO 2004/028225 A1 | 4/2004 |
| WO | 2004/106437 A1 | 12/2004 |

OTHER PUBLICATIONS

International Search Report dated May 2, 2019 relating to PCT/EP2019/054676, 4 pages.
Written Opinion dated May 2, 2019 relating to PCT/EP2019/054676, 6 pages.

* cited by examiner

INKJET INKS FOR MANUFACTURING PRINTED CIRCUIT BOARDS

REFERENCE TO RELATED APPLICATIONS

This application is a 371 National Stage Application of PCT/EP2019/054676, filed Feb. 26, 2019, which claims the benefit of European Application No. 18159698.2, filed Mar. 2, 2018, the contents of which are incorporated by reference herein in their entirety.

TECHNICAL FIELD OF THE INVENTION

The present invention relates to a radiation curable inkjet ink that may be used in the manufacturing of PCBs, for example as an etch resistant inkjet ink, and methods of manufacturing such PCBs.

BACKGROUND ART FOR THE INVENTION

The production workflow of printed circuit boards (PCBs) is gradually shifting from the standard workflow towards a digital workflow to reduce the amount of process steps and lowering the cost and the environmental impact of the production of PCBs, especially for short run productions. Inkjet is one of the preferred digital manufacturing technologies in different steps of the PCB manufacturing process going from etch resist over solder mask to legend printing. Preferred inkjet inks therefore are UV curable ink jet inks.

In the different production steps, adhesion of the inkjet inks towards different substrates is of crucial importance. To maximize the adhesion performance, adhesion promoters are often required.

In etch resist applications, the adhesion has to be balanced with the stripping performance of the jetted and cured etch resist. Upon stripping, the etch resist has to be completely removed from the metal surface in an alkaline medium, requiring a well-controlled amount of deprotonatable functional groups.

Several classes of adhesion promoters have been disclosed in the prior art, most of them acidic in nature.

WO2004/026977 (Avecia) discloses a non-aqueous etch resistant inkjet ink comprising 1 to 30 wt % of an acrylate functional monomer containing one or more acidic group as an adhesion promoter and dissolution promoter during stripping.

WO2004/106437 (Avecia) discloses an etch resistant inkjet ink preferably comprising (meth)acrylate acid adhesion promoters, such as (meth)acrylated carboxylic acids, (meth)acrylated phosphoric acid esters and (meth)acrylated sulphonic acids.

When using an acidic adhesion promoter, that single compound has to control both the adhesion during etching and the stripping behavior. Therefore, it would be advantageous to use a neutral adhesion promoter in combination with a stripping controlling monomer, allowing optimization of both etching performance and stripping performance independently from each other.

Several classes of neutral adhesion promoters have been disclosed, often in dental applications.

In DE10063332 (Girrback Dental GmbH) acrylated thioethers have been reported as adhesion promoters in dental applications. Acrylated thioethers have also been disclosed in JP2010006977 (FujiFilm Corporation) as monomers in inkjet inks in combination with a specific sensitizer mainly targeting at jetting on synthetic resins. However, none of the disclosed compositions can be used as an etch resist inkjet ink in PCB production.

There is thus a need for alternative adhesion promotors for radiation curable inkjet inks for use in a PCB manufacturing process.

SUMMARY OF THE INVENTION

It is an object of the invention to provide a radiation curable inkjet ink for use in a PCB manufacturing process characterized by a good adhesion while maintaining excellent jetting, stability and stripping performance.

The object of the invention is realized by the method of manufacturing a PCB as defined in claim 1 and the radiation curable inkjet ink as defined in claim 13.

It has been found that a radiation curable composition comprising an adhesion promoter according to Formula I shows excellent adhesion while maintaining excellent jetting, stability and stripping performance.

Further objects of the invention will become apparent from the description hereinafter.

DETAILED DESCRIPTION OF THE INVENTION

Definitions

The term "monofunctional" in e.g. monofunctional polymerizable compound means that the polymerizable compound includes one polymerizable group.

The term "difunctional" in e.g. difunctional polymerizable compound means that the polymerizable compound includes two polymerizable groups.

The term "polyfunctional" in e.g. polyfunctional polymerizable compound means that the polymerizable compound includes more than two polymerizable groups.

The term "alkyl" means all variants possible for each number of carbon atoms in the alkyl group i.e. methyl, ethyl, for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethyl-propyl and 2-methyl-butyl, etc.

Unless otherwise specified a substituted or unsubstituted alkyl group is preferably a $C_1$ to $C_6$-alkyl group.

Unless otherwise specified a substituted or unsubstituted alkenyl group is preferably a $C_2$ to $C_6$-alkenyl group.

Unless otherwise specified a substituted or unsubstituted alkynyl group is preferably a $C_2$ to $C_6$-alkynyl group.

Unless otherwise specified a substituted or unsubstituted aralkyl group is preferably a phenyl or naphthyl group including one, two, three or more $C_1$ to $C_6$-alkyl groups.

Unless otherwise specified a substituted or unsubstituted alkaryl group is preferably a $C_7$ to $C_{20}$-alkyl group including a phenyl group or naphthyl group.

Unless otherwise specified a substituted or unsubstituted aryl group is preferably a phenyl group or naphthyl group Unless otherwise specified a substituted or unsubstituted heteroaryl group is preferably a five- or six-membered ring substituted by one, two or three oxygen atoms, nitrogen atoms, sulphur atoms, selenium atoms or combinations thereof.

The term "substituted", in e.g. substituted alkyl group means that the alkyl group may be substituted by other atoms than the atoms normally present in such a group, i.e. carbon and hydrogen. For example, a substituted alkyl group may include a halogen atom or a thiol group. An unsubstituted alkyl group contains only carbon and hydrogen atoms Unless otherwise specified a substituted alkyl group, a substituted alkenyl group, a substituted alkynyl group, a substituted aralkyl group, a substituted alkaryl group, a substituted aryl and a substituted heteroaryl group are preferably substituted by one or more constituents selected from the group consisting of methyl, ethyl, n-propyl, isopropyl, n-butyl, isobutyl and tertiary-butyl, ester, amide, ether, thioether, ketone, aldehyde, sulfoxide, sulfone, sulfonate ester, sulphonamide, —Cl, —Br, —I, —OH, —SH, —CN and —NO$_2$.

Method of Manufacturing a Printed Circuit Board

The method of manufacturing a Printed Circuit Board (PCB) according to the present invention comprises at least one inkjet printing step is, characterized in that in the inkjet printing step a radiation curable inkjet ink comprising an adhesion promoter as described below is used.

According to a preferred embodiment, the method of manufacturing a PCB comprises an inkjet printing step wherein an etch resist is provided on a metal surface, preferably a copper surface.

The etch resist is provided on the metal surface by jetting and curing the radiation curable inkjet ink on the metal surface thereby forming a protected area of the metal surface. Metal from an unprotected area of the metal surface is then removed by etching. After etching, at least part of the etch resist is removed from the protected area of the metal surface.

The inkjet printing step wherein an etch resist is provided preferably comprises a radiation curable inkjet ink including an adhesion promoter as described below and a polymerizable compound having a pKa of at least 2.5.

The metal surface is preferably a metal foil or sheet attached to a substrate.

There is no real limitation on the type of substrate bonded to the metal sheet as long as it is non-conductive. The substrates may be made of a ceramic, glass or plastics, such as polyimides.

The metal sheet usually has a thickness between 9 and 105 µm.

There is no limitation on the nature of the metal surface. The metal surfaces preferably consist of copper, aluminium, nickel, iron, tin, titanium or zinc, but may be also alloys including these metals. In a very preferred embodiment, the metal surface is made of copper. Copper has a high electrical conductivity and is a relatively cheap metal, making it very suitable for making printed circuit boards.

The method may also be used for manufacturing a decorative etched metal panel.

The metal surface used may be selected from the metals described above for the embodiment wherein conductive patterns are prepared. In this case, preferably a solid metal panel is used. However, also a metal foil attached to a substrate may be used. There is no real limitation on the type of substrate bonded to the metal foil. The substrates may be made of a ceramic, glass or plastics, or even a second (cheaper) metal plate. The metal may also be an alloy.

Such a decorative metal panel may serve a purpose other than being purely decorative, such as providing information. For example, an aluminium name plate wherein the etch resistant radiation curable inkjet ink was printed as information, such as a name of a person or a company, and then removed to result in a glossy shiny name on a mat etched background, is also considered a decorative metal panel including a decorative element. Etching causes a change in optical properties of a metal surface, such as a change of gloss. After removal of the cured radiation curable inkjet ink from the metal surface an aesthetic effect is created between the etched and the non-etched metal surface.

In a preferred embodiment of the inkjet printing method, the metal surface is cleaned before printing the radiation curable inkjet ink. This is especially desirable when the metal surface is handled by hand and no gloves are worn. The cleaning removes dust particles and grease which can interfere in the adhesion of the radiation curable inkjet ink to the metal surface. In PCB the copper is often cleaned by microetching. The oxide layer of the copper is removed and roughness introduced in order to improve the adhesion.

The inkjet method may also be used for manufacturing a decorative etched glass panel. Such a method is disclosed in for example WO2013/189762 (AGC).

According to another preferred embodiment, the method of manufacturing a PCB comprises an inkjet printing step wherein a solder mask is provided.

The solder mask is provided by jetting and curing the radiation curable inkjet ink typically on a dielectric substrate containing an electrically conductive pattern.

A heat treatment is preferably applied to the jetted and cured radiation curable inkjet ink. The heat treatment is preferably carried out at a temperature between 80° C. and 250° C. The temperature is preferably not less than 100° C., more preferably not less than 120° C. To prevent charring of the solder mask, the temperature is preferably not greater than 200° C., more preferably not greater than 160° C.

The thermal treatment is typically carried out between 15 and 90 minutes.

The purpose of the thermal treatment is to further increase the polymerization degree of the solder mask.

This further polymerization during the thermal treatment may be accelerated by adding radical initiators, blocked thermal acid generators, blocked acid catalysts and/or thermosetting compounds which promote thermal curing of polymers, such as peroxides, azo compounds, acid anhydrides, and phenolics, to the solder mask inkjet ink.

The dielectric substrate of the electronic device may be any non-conductive material. The substrate is typically a paper/resin composite or a resin/fibre glass composite, a ceramic substrate, a polyester or a polyimide.

The electrically conductive pattern is typically made from any metal or alloy which is conventionally used for preparing electronic devices such as gold, silver, palladium, nickel/gold, nickel, tin, tin/lead, aluminium, tin/aluminium and copper. The electrically conductive pattern is preferably made from copper.

The radiation curable solder mask inkjet ink may be cured in both embodiments by exposing the ink to actinic radiation, such as electron beam or ultraviolet (UV) radiation. Preferably the radiation curable inkjet ink is cured by UV radiation, more preferably using UV LED curing.

The method of manufacturing a PCB may comprise two, three or more inkjet printing steps. For example the method may comprise two inkjet printing steps wherein an etch resist is provided on a metal surface in one inkjet printing step and wherein a solder mask is provided on a dielectric substrate containing an electrically conductive pattern in another inkjet printing step.

A third inkjet printing step may be used for legend printing.

Etching

Etching of a metal surface, as in step b) of the inkjet printing method, is performed by using an etchant. The etchant is preferably an aqueous solution having a pH<3 or wherein 8<pH<10.

In a preferred embodiment, the etchant is an acid aqueous solution having a pH of less than 2. The acid etchant preferably includes at least one acid selected from the group consisting of nitric acid, picric acid, hydrochloric acid, hydrofluoric acid and sulphuric acid.

Preferred etchants known in the art include Kalling's No. 2, ASTM No. 30, Kellers Etch, Klemm's Reagent, Kroll's Reagent, Marble's Reagent, Murakami's Reagent, Picral and Vilella's Reagent.

In another preferred embodiment, the etchant is an alkaline aqueous solution having a pH of no more than 9. The alkaline etchant preferably includes at least one base selected from the group consisting of ammonia or ammonium hydroxide, potassium hydroxide and sodium hydroxide.

The etchant may also contain a metal salt such as copper dichloride, copper sulphate, potassium ferricyanide and iron trichloride.

Etching of a metal surface in PCB applications is preferably performed in a time frame of seconds to a few minutes, more preferably 5 to 200 seconds. Etching is preferably performed at a temperature between 35 and 60° C.

The etching time of a metal surface in other applications, such as in the manufacture or decorative metal panels, may be substantially longer, depending on the type and amount of metal that has to be removed during the etch step. Etching times may be more then 15, 30 or even 60 minutes.

In the method wherein a glass surface is etched, the etching solution is preferably an aqueous solution of hydrofluoric acid. Typically, the etching solution has a pH between 0 and 5.

Etching is preferably followed by rinsing with water to remove any residual etchant.

Stripping

After etching, the cured radiation curable inkjet ink must at least partially be removed from the metal surface, so that e.g. electric or electronic devices can make contact with the remaining metal surface (conductive pattern) or that the decorative feature of an etched metal panel becomes fully visible. For example, an electronic component such as a transistor must be able to make electrical contacts with the conductive (copper) pattern on the printed circuit board. In a preferred embodiment, the cured radiation curable inkjet ink is completely removed from the metal surface.

In a preferred embodiment, the cured radiation curable inkjet ink is removed from the protected area in step c) by an alkaline stripping bath. Such an alkaline stripping bath is usually an aqueous solution with a pH>10.

In another embodiment, the cured radiation curable inkjet ink is removed from the protected area in step c) by dry delamination. This technique of "dry stripping" is currently unknown in the art of manufacturing printed circuit boards and introduces several ecological and economical advantages in the manufacturing process. Dry stripping not only eliminates the need of a corrosive alkaline stripping bath and its inherent liquid waste, but also allows for a higher throughput. Dry stripping can be implemented, for example, by using an adhesive foil and a roll-to-roll laminator-delaminator. The adhesive foil is first laminated with its adhesive side onto the cured radiation curable inkjet ink present on the metal surface and subsequently delaminated thereby removing the cured radiation curable inkjet ink from the metal surface. Delamination by a roll-to-roll laminator-delaminator can be performed in seconds, while alkaline stripping can take minutes.

Radiation Curable Inkjet Ink

The radiation curable inkjet ink of the present invention includes an adhesion promoter as described below.

The radiation curable inkjet ink preferably also comprises a polymerizable compound having a pKa of at least 2.5.

The radiation curable inkjet ink may be cured by any type of radiation, for example by electron-beam radiation, but is preferably cured by UV radiation, more preferably by UV radiation from UV LEDs. The radiation curable inkjet ink is thus preferably a UV curable inkjet ink.

For reliable industrial inkjet printing, the viscosity of the radiation curable inkjet inks is preferably no more than 20 mPa·s at 45° C., more preferably between 1 and 18 mPa·s at 45° C., and most preferably between 4 and 14 mPa·s at 45° C.

For good image quality and adhesion, the surface tension of the radiation curable inkjet inks is preferably in the range of 18 mN/m to 70 mN/m at 25° C., more preferably in the range of about 20 mN/m to about 40 mN/m at 25° C.

The radiation curable inkjet ink may further comprise other polymerizable compounds, colorants, polymeric dispersants, a photoiniator or photoinitiating system, a polymerization inhibitor, a flame retardant, or a surfactant.

Adhesion Promoter

The adhesion promoter has a chemical structure according to Formula I,

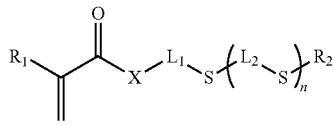

Formula I wherein

X is selected from the group consisting of O and $NR_3$, $L_1$ and $L_2$ independently represent a divalent linking group comprising from 2 to 20 carbon atoms, $R_1$ is selected from the group consisting of a hydrogen, a substituted or unsubstituted alkyl group and a substituted or unsubstituted aryl group, $R_2$ is selected from the group consisting of a substituted or unsubstituted alkyl group, a substituted or unsubstituted alkenyl group, a substituted or unsubstituted alkynyl group, a substituted or unsubstituted alkaryl group, a substituted or unsubstituted aralkyl group and a substituted or unsubstituted (hetero)aryl group, $R_3$ is selected from the group consisting of a hydrogen, a substituted or unsubstituted alkyl group, a substituted or unsubstituted alkenyl group, a substituted or unsubstituted alkynyl group, a substituted or unsubstituted alkaryl group, a substituted or unsubstituted aralkyl group and a substituted or unsubstituted (hetero)aryl group, n represents an integer from 0 to 4, any of $L_1$, $L_2$ and $R_2$ may represent the necessary atoms to form a 5 to 8 membered ring.

X preferably represents an oxygen.

$R_1$ is preferably selected from the group consisting of a hydrogen and an alkyl group, a hydrogen and a methyl group being more preferred, a hydrogen being most preferred.

$L_1$ and $L_2$ preferably represent a substituted or unsubstituted alkylene group having from 2 to 20 carbon atoms, more preferably from 2 to 10 carbon atoms.

Preferably, n represent an integer from 1 to 4, more preferably n represent 0 or 1, most preferably n represents 1.

R₂ preferably comprises at least one polymerizable group selected from the group consisting of an acrylate, a methacrylate, an acrylamide and a methacrylamide, an acrylate and a methacrylate being more preferred, an acrylate being most preferred.

In a particularly preferred embodiment, the adhesion promoter has a chemical formula according to Formula II,

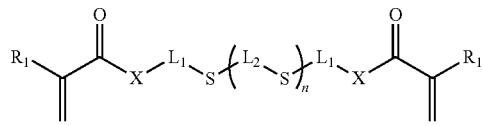

Formula II wherein
X, $R_1$, $L_1$, $L_2$ and n are as defined as above.

Examples of thioether based adhesion promoters according to the present invention are given in Table 1.

TABLE 1

TABLE 1-continued
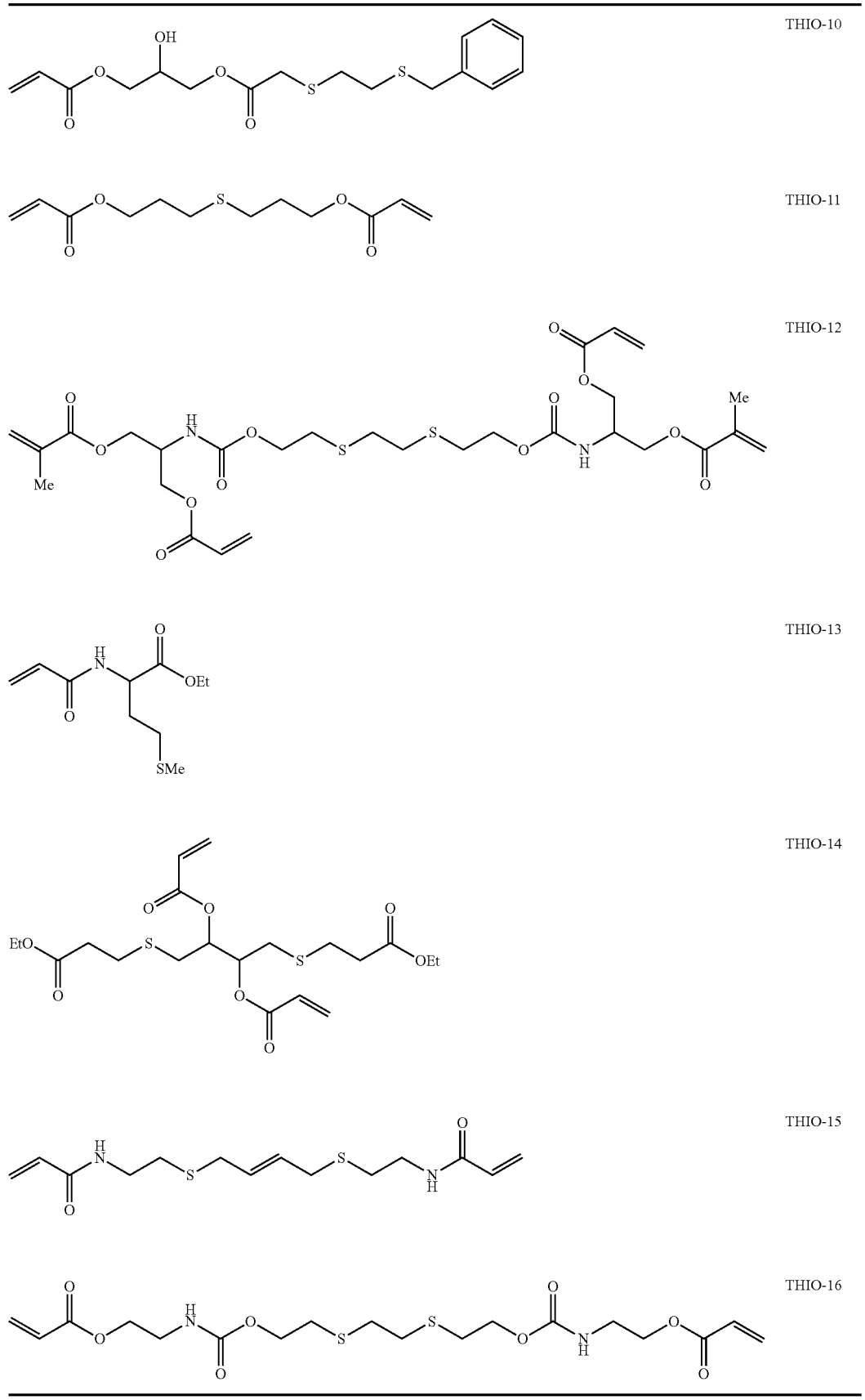

The amount of adhesion promoter in the radiation curable inkjet ink is preferably between 0.1 and 20 wt %, more preferably between 0.5 and 15 wt %, most preferably between 1 and 10 wt %, relative to the total weight of the inkjet ink.

When the amount is too low, the adhesion of the inkjet ink to the metal surface may be insufficient, when the amount is too high, the ink viscosity may increase and the shelf life may become more critical.

Polymerizable Compound Having a pKa of at Least 2.5.

The radiation curable inkjet ink preferably comprises a polymerizable compound having a pKa of at least 2.5, preferably at least 4, more preferably at least 5, most preferably at least 7.

The polymerizable compound having a pKa of at least 2.5 is preferably a phenolic monomer.

The phenolic monomer is preferably selected from the group consisting of a phenolic acrylate, a phenolic methacrylate, a phenolic acrylamide and a phenolic methacrylamide, an acrylate and a methacrylate being more preferred. Examples of phenolic monomers according to the present invention are given in Table 2.

TABLE 2

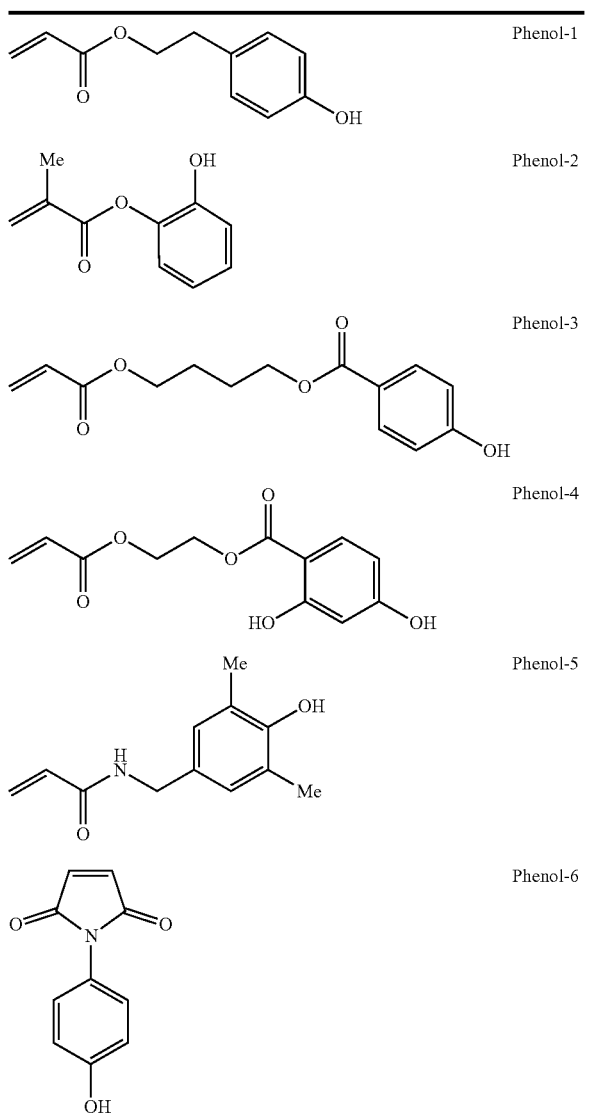

TABLE 2-continued

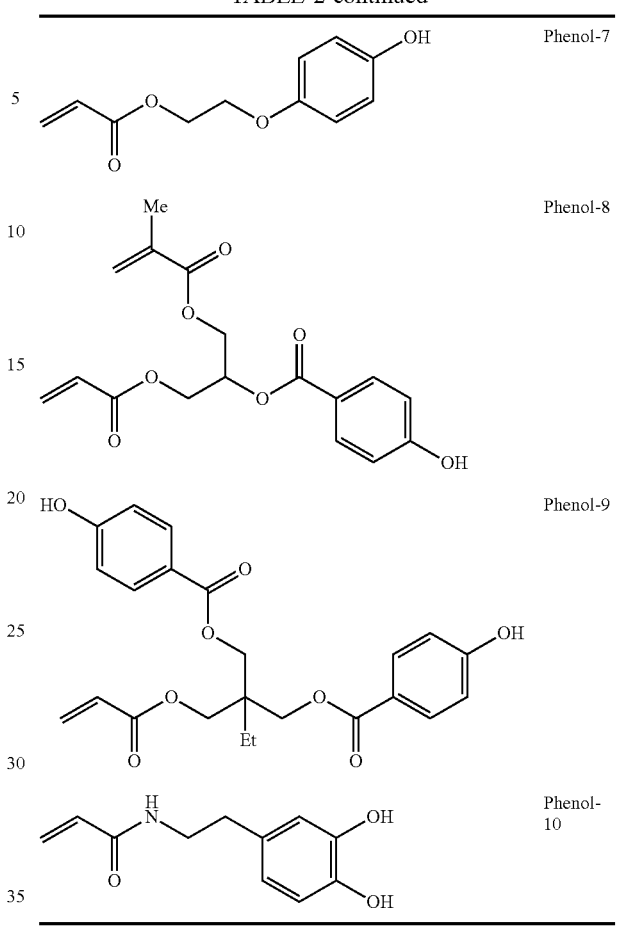

The amount of the acidic polymerizable compound described above in the radiation curable inkjet ink is preferably between 0.5 and 25 wt %, more preferably between 1 and 15 wt %, most preferably between 2.5 and 10 wt %, relative to the total weight of the inkjet ink.

When the amount is too low, the water resistance will not be sufficient, when the amount is too high, the etch resistance will become worse.

Other Polymerizable Compounds

Besides the adhesion promoter described above, the radiation curable inkjet ink preferably comprise other polymerizable compounds.

The other polymerizable compounds may be monomers, oligomers and/or prepolymers. These monomers, oligomers and/or prepolymers may possess different degrees of functionality. A mixture including combinations of mono-, di-, tri- and higher functionality monomers, oligomers and/or prepolymers may be used. The viscosity of the radiation curable inkjet ink may be adjusted by varying the ratio between the monomers and oligomers.

Particularly preferred monomers and oligomers are those listed in [0106] to [0115] in EP-A 1911814.

Other preferred monomers and oligomers are those disclosed in EP-As 2809735, 2725075, 2915856, 3000853 and 3119170 (all from Agfa Gevaert NV).

A radiation curable composition for use in the inkjet printing step wherein an etch resist is provided preferably comprises a monomer according to Formula III,

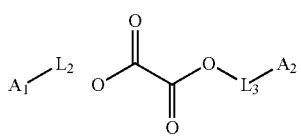

Formula III wherein $A_1$ and $A_2$ are independently selected from the group consisting of an acrylate, a methacrylate, an acrylamide and a methacrylamide, and $L_2$ and $L_3$ represent a divalent linking group including 2 to 10 carbon atoms.

Preferably, $A_1$ and $A_2$ are independently selected from the group consisting of an acrylate and a methacrylate, an acrylate being particularly preferred.

Specific examples of monomers according to Formula III are disclosed in paragraph [0056] of EP-A 2703180 (Agfa-Gevaert N.V.).

Colorants

The radiation curable inkjet may be a substantially colourless inkjet ink, but preferably the radiation curable inkjet includes at least one colorant. The colorant makes the temporary mask clearly visible to the manufacturer of conductive patters, allowing a visual inspection of quality.

The colorant may be a pigment or a dye, but is preferably a dye that is not bleached by an UV curing step during the inkjet printing process of the radiation curable inkjet. The pigments may be black, white, cyan, magenta, yellow, red, orange, violet, blue, green, brown, mixtures thereof, and the like. A colour pigment may be chosen from those disclosed by HERBST, Willy, et al. Industrial Organic Pigments, Production, Properties, Applications. 3rd edition. Wiley-VCH, 2004. ISBN 3527305769.

Suitable pigments are disclosed in paragraphs [0128] to [0138] of WO2008/074548.

Pigment particles in inkjet inks should be sufficiently small to permit free flow of the ink through the inkjet-printing device, especially at the ejecting nozzles. It is also desirable to use small particles for maximum colour strength and to slow down sedimentation. Most preferably, the average pigment particle size is no larger than 150 nm. The average particle size of pigment particles is preferably determined with a Brookhaven Instruments Particle Sizer BI90plus based upon the principle of dynamic light scattering.

Generally dyes exhibit a higher light fading than pigments, but cause no problems on jettability. It was found that anthraquinone dyes exhibit only minor light fading under the normal UV curing conditions used in UV curable inkjet printing.

In a preferred embodiment, the colorant in the radiation curable inkjet ink is an anthraquinone dye, such as Macrolex™ Blue 3R (CASRN 325781-98-4) from LANXESS.

Other preferred dyes include crystal violet and a copper phthalocyanine dye.

In a preferred embodiment, the colorant is present in an amount of 0.5 to 6.0 wt %, more preferably 1.0 to 2.5 wt %, based on the total weight of the radiation curable inkjet ink.

Polymeric Dispersants

If the colorant in the radiation curable inkjet is a pigment, then the radiation curable inkjet preferably contains a dispersant, more preferably a polymeric dispersant, for dispersing the pigment.

Suitable polymeric dispersants are copolymers of two monomers but they may contain three, four, five or even more monomers. The properties of polymeric dispersants depend on both the nature of the monomers and their distribution in the polymer. Copolymeric dispersants preferably have the following polymer compositions:

statistically polymerized monomers (e.g. monomers A and B polymerized into ABBAABAB);

alternating polymerized monomers (e.g. monomers A and B polymerized into ABABABAB);

gradient (tapered) polymerized monomers (e.g. monomers A and B polymerized into AAABAABBABBB);

block copolymers (e.g. monomers A and B polymerized into AAAAABBBBBB) wherein the block length of each of the blocks (2, 3, 4, 5 or even more) is important for the dispersion capability of the polymeric dispersant;

graft copolymers (graft copolymers consist of a polymeric backbone with polymeric side chains attached to the backbone); and mixed forms of these polymers, e.g. blocky gradient copolymers.

Suitable polymeric dispersants are listed in the section on "Dispersants", more specifically [0064] to [0070] and [0074] to [0077], in EP-A 1911814.

Commercial examples of polymeric dispersants are the following:

DISPERBYK™ dispersants available from BYK CHEMIE GMBH;

SOLSPERSE™ dispersants available from NOVEON;

TEGO™ DISPERS™ dispersants from EVONIK;

EDAPLAN™ dispersants from MUNZING CHEMIE;

ETHACRYL™ dispersants from LYONDELL;

GANEX™ dispersants from ISP;

DISPEX™ and EFKA™ dispersants from CIBA SPECIALTY CHEMICALS INC;

DISPONER™ dispersants from DEUCHEM; and

JONCRYL™ dispersants from JOHNSON POLYMER.

Photoinitiators and Photoinitiating Systems

The radiation curable inkjet preferably contains at least one photoinitiator, but may contain a photoinitiating system including a plurality of photoinitiators and/or co-initiators.

The photoinitiator in the radiation curable inkjet is preferably a free radical initiator, more specifically a Norrish type I initiator or a Norrish type II initiator. A free radical photoinitiator is a chemical compound that initiates polymerization of monomers and oligomers when exposed to actinic radiation by the formation of a free radical. A Norrish Type I initiator is an initiator which cleaves after excitation, yielding the initiating radical immediately. A Norrish type II-initiator is a photoinitiator which is activated by actinic radiation and forms free radicals by hydrogen abstraction from a second compound that becomes the actual initiating free radical. This second compound is called a polymerization synergist or co-initiator. Both type I and type II photoinitiators can be used in the present invention, alone or in combination.

Suitable photoinitiators are disclosed in CRIVELLO, J. V., et al. Photoinitiators for Free Radical Cationic and Anionic Photopolymerization. 2nd edition. Edited by BRADLEY, G. London, UK: John Wiley and Sons Ltd, 1998. p. 287-294.

Specific examples of photoinitiators may include, but are not limited to, the following compounds or combinations thereof: benzophenone and substituted benzophenones, 1-hydroxycyclohexyl phenyl ketone, thioxanthones such as isopropylthioxanthone, 2-hydroxy-2-methyl-1-phenylpropan-1-one, 2-benzyl-2-dimethylamino-(4-morpholinophenyl) butan-1-one, benzyl dimethylketal, bis (2,6-dimethylbenzoyl)-2,4,4-trimethylpentylphosphine oxide, 2,4,6 trimethylbenzoyl-diphenylphosphine oxide, 2,4,6-trimethoxybenzoyldiphenylphosphine oxide, 2-methyl-1-[4-(methylthio)phenyl]-2-morpholinopropan-1-one, 2,2-dimethoxy-1, 2-diphenylethan-1-one or 5,7-diiodo-3-butoxy-6-fluorone.

Suitable commercial photoinitiators include Irgacure™ 184, Irgacure™ 500, Irgacure™ 369, Irgacure™ 1700, Irgacure™ 651, Irgacure™ 819, Irgacure™ 1000, Irgacure™ 1300, Irgacure™ 1870, Darocur™ 1173, Darocur™ 2959, Darocur™ 4265 and Darocur™ ITX available from CIBA SPECIALTY CHEMICALS, Lucerin™ TPO available from BASF AG, Esacure™ KT046, Esacure™ KIP150, Esacure™ KT37 and Esacure™ EDB available from LAMBERTI, H-Nu™ 470 and H-Nu™ 470X available from SPECTRA GROUP Ltd.

The photoinitiator may be a so-called diffusion hindered photoinitiator. A diffusion hindered photoinitiator is a photoinitiator which exhibits a much lower mobility in a cured ink layer than a monofunctional photoinitiator, such as benzophenone. Several methods can be used to lower the mobility of the photoinitiator. One way is to increase the molecular weight of the photoinitiators so that the diffusion speed is reduced, e.g. polymeric photoinitiators. Another way is to increase its reactivity so that it is built into the polymerizing network, e.g. multifunctional photoinitiators (having 2, 3 or more photoinitiating groups) and polymerizable photoinitiators.

The diffusion hindered photoinitiator for the radiation curable inkjet is preferably selected from the group consisting of non-polymeric multifunctional photoinitiators, oligomeric or polymeric photoinitiators and polymerizable photoinitiators. Most preferably the diffusion hindered photoinitiator is a polymerizable initiator or a polymeric photoinitiator.

A preferred diffusion hindered photoinitiator contains one or more photoinitiating functional groups derived from a Norrish type 1-photoinitiator selected from the group consisting of benzoinethers, benzil ketals, α,α-dialkoxyacetophenones, α-hydroxyalkylphenones, α-aminoalkylphenones, acylphosphine oxides, acylphosphine sulphides, α-haloketones, α-halosulfones and phenylglyoxalates.

A preferred diffusion hindered photoinitiator contains one or more photoinitiating functional groups derived from a Norrish type II-initiator selected from the group consisting of benzophenones, thioxanthones, 1,2-diketones and anthraquinones.

Suitable diffusion hindered photoinitiators are also those disclosed in EP-A 2065362 in paragraphs [0074] and [0075] for difunctional and multifunctional photoinitiators, in paragraphs [0077] to [0080] for polymeric photoinitiators and in paragraphs [0081] to [0083] for polymerizable photoinitiators.

A preferred amount of photoinitiator is 0.1-20 wt %, more preferably 2-15 wt %, and most preferably 3-10 wt % of the total weight of the radiation curable inkjet.

In order to increase the photosensitivity further, the radiation curable inkjet may additionally contain co-initiators. Suitable examples of co-initiators can be categorized in three groups: 1) tertiary aliphatic amines such as methyldiethanolamine, dimethylethanolamine, triethanolamine, triethylamine and N-methylmorpholine; (2) aromatic amines such as amylparadimethyl-aminobenzoate, 2-n-butoxyethyl-4-(dimethylamino) benzoate, 2-(dimethylamino)-ethylbenzoate, ethyl-4-(dimethylamino)benzoate, and 2-ethylhexyl-4-(dimethylamino)benzoate; and (3) (meth)acrylated amines such as dialkylamino alkyl(meth)acrylates (e.g., diethylaminoethylacrylate) or N-morpholinoalkyl-(meth)acrylates (e.g., N-morpholinoethyl-acrylate). The preferred co-initiators are aminobenzoates.

When one or more co-initiators are included into the radiation curable inkjet ink, preferably these co-initiators are diffusion hindered for safety reasons.

A diffusion hindered co-initiator is preferably selected from the group consisting of non-polymeric di- or multifunctional co-initiators, oligomeric or polymeric co-initiators and polymerizable co-initiators. More preferably the diffusion hindered co-initiator is selected from the group consisting of polymeric co-initiators and polymerizable co-initiators. Most preferably the diffusion hindered co-initiator is a polymerizable co-initiator having at least one (meth)acrylate group, more preferably having at least one acrylate group.

The radiation curable inkjet ink preferably includes a polymerizable or polymeric tertiary amine co-initiator.

Preferred diffusion hindered co-initiators are the polymerizable co-initiators disclosed in EP-A 2053101 in paragraphs [0088] and [0097].

The radiation curable inkjet inks preferably includes the (diffusion hindered) co-initiator in an amount of 0.1 to 20 wt %, more preferably in an amount of 0.5 to 15 wt %, most preferably in an amount of 1 to 10 wt % of the total weight of the radiation curable inkjet ink.

Polymerization Inhibitors

The radiation curable inkjet ink may contain at least one inhibitor for improving the thermal stability of the ink.

Suitable polymerization inhibitors include phenol type antioxidants, hindered amine light stabilizers, phosphor type antioxidants, hydroquinone monomethyl ether commonly used in (meth)acrylate monomers, and hydroquinone, t-butyl-catechol, pyrogallol, 2,6-di-tert.butyl-4-methylphenol (=BHT) may also be used.

Suitable commercial inhibitors are, for example, Sumilizer™ GA-80, Sumilizer™ GM and Sumilizer™ GS produced by Sumitomo Chemical Co. Ltd.; Genorad™ 16, Genorad™18 and Genorad™ 20 from Rahn AG; Irgastab™UV10 and Irgastab™ UV22, Tinuvin™ 460 and CGS20 from Ciba Specialty Chemicals; Floorstab™ UV range (UV-1, UV-2, UV-5 and UV-8) from Kromachem Ltd, Additol™ S range (S100, S110, S120 and S130) from Cytec Surface Specialties.

The inhibitor is preferably a polymerizable inhibitor.

Since excessive addition of these polymerization inhibitors may lower the curing speed, it is preferred that the amount capable of preventing polymerization is determined prior to blending. The amount of a polymerization inhibitor is preferably lower than 5 wt %, more preferably lower than 3 wt % of the total radiation curable inkjet ink.

Surfactants

The radiation curable inkjet may contain at least one surfactant, but preferably no surfactant is present. If no surfactant is present, the radiation curable inkjet ink does not spread well on the metal sheet, allowing the generation of thin conductive lines.

The surfactant can be anionic, cationic, non-ionic, or zwitter-ionic and is usually added in a total quantity less than 1 wt % based on the total weight of the radiation curable inkjet ink.

Suitable surfactants include fluorinated surfactants, fatty acid salts, ester salts of a higher alcohol, alkylbenzene sulfonate salts, sulfosuccinate ester salts and phosphate ester salts of a higher alcohol (for example, sodium dodecylbenzenesulfonate and sodium dioctylsulfosuccinate), ethylene oxide adducts of a higher alcohol, ethylene oxide adducts of an alkylphenol, ethylene oxide adducts of a polyhydric alcohol fatty acid ester, and acetylene glycol and ethylene oxide adducts thereof (for example, polyoxyethylene nonylphenyl ether, and SURFYNOL™ 104, 104H, 440, 465 and TG available from AIR PRODUCTS & CHEMICALS INC.).

Preferred surfactants are selected from fluoric surfactants (such as fluorinated hydrocarbons) and silicone surfactants. The silicone surfactants are preferably siloxanes and can be alkoxylated, polyether modified, polyether modified hydroxy functional, amine modified, epoxy modified and other modifications or combinations thereof. Preferred siloxanes are polymeric, for example polydimethylsiloxanes.

Preferred commercial silicone surfactants include BYK™ 333 and BYK™ UV3510 from BYK Chemie.

In a preferred embodiment, the surfactant is a polymerizable compound.

Preferred polymerizable silicone surfactants include a (meth)acrylated silicone surfactant. Most preferably the (meth)acrylated silicone surfactant is an acrylated silicone surfactant, because acrylates are more reactive than methacrylates.

In a preferred embodiment, the (meth)acrylated silicone surfactant is a polyether modified (meth)acrylated polydimethylsiloxane or a polyester modified (meth)acrylated polydimethylsiloxane.

Preferably the surfactant is present in the radiation curable inkjet ink in an amount of 0 to 3 wt % based on the total weight of the radiation curable inkjet ink.

Preparation of Inkjet Inks

The preparation of pigmented radiation curable inkjet inks is well-known to the skilled person. Preferred methods of preparation are disclosed in paragraphs [0076] to [0085] of WO2011/069943.

Inkjet Printing Devices

The radiation curable inkjet ink may be jetted by one or more print heads ejecting small droplets in a controlled manner through nozzles onto a substrate, which is moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with ink. When the voltage is again removed, the ceramic expands to its original shape, ejecting a drop of ink from the print head. However the inkjet printing method according to the present invention is not restricted to piezoelectric inkjet printing. Other inkjet print heads can be used and include various types, such as a continuous type.

The inkjet print head normally scans back and forth in a transversal direction across the moving ink-receiver surface. Often the inkjet print head does not print on the way back. Bi-directional printing is preferred for obtaining a high areal throughput. Another preferred printing method is by a "single pass printing process", which can be performed by using page wide inkjet print heads or multiple staggered inkjet print heads which cover the entire width of the metal plate. In a single pass printing process the inkjet print heads usually remain stationary and the metal substrate is transported under the inkjet print heads.

Curing Devices

The radiation curable inkjet ink can be cured by exposing them to actinic radiation, such as electron beam or ultraviolet radiation. Preferably the radiation curable inkjet ink is cured by ultraviolet radiation, more preferably using UV LED curing.

In inkjet printing, the curing means may be arranged in combination with the print head of the inkjet printer, travelling therewith so that the curable liquid is exposed to curing radiation very shortly after been jetted.

In such an arrangement, with the exception of UV LEDs, it can be difficult to provide a small enough radiation source connected to and travelling with the print head. Therefore, a static fixed radiation source may be employed, e.g. a source of curing UV-light, connected to the radiation source by means of flexible radiation conductive means such as a fibre optic bundle or an internally reflective flexible tube.

Alternatively, the actinic radiation may be supplied from a fixed source to the radiation head by an arrangement of mirrors including a mirror upon the radiation head.

The source of radiation may also be an elongated radiation source extending transversely across the substrate to be cured. It may be adjacent the transverse path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:

UV-A: 400 nm to 320 nm
UV-B: 320 nm to 290 nm
UV-C: 290 nm to 100 nm.

In a preferred embodiment, the radiation curable inkjet ink is cured by UV LEDs. The inkjet printing device preferably contains one or more UV LEDs preferably with a wavelength larger than 360 nm, preferably one or more UV LEDs with a wavelength larger than 380 nm, and most preferably UV LEDs with a wavelength of about 395 nm.

Furthermore, it is possible to cure the ink image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

For facilitating curing, the inkjet printing device often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1200 ppm.

EXAMPLES

Materials

All materials used in the following examples were readily available from standard sources such as ALDRICH CHEMICAL Co. (Belgium) and ACROS (Belgium) unless otherwise specified. The water used was deionized water.

SR606A is a mixture of 80-90% of neopentylglycol hydroxypivalate diacrylate and 10-20% neopentylglycol diacrylate available as Sartomer™ SR606A from ARKEMA.

ACMO is acryloyl morpholine available from RAHN.

ITX is an isomeric mixture of 2- and 4-isopropylthioxanthone available as Darocur™ ITX from BASF.

TPO-L is ethyl (2,4,6-trimethylbenzoyl) phenyl phosphinate, a photoinitiator available as Speedcure™ TPO-L from LAMBSON.

EPD is ethyl 4-dimethyaminobenzoate available as Genocure™ EPD from RAHN.

CEA is 2-carboxyethyl acrylate from ALDRICH.

CN146 is (2-acryloyloxyethyl) phthalate from ARKEMA.

INHIB is a mixture forming a polymerization inhibitor having a composition according to Table 3

TABLE 3

| Component | wt % |
|---|---|
| DPGDA | 82.4 |
| p-methoxyphenol | 4.0 |
| 2,6-di-tert-butyl-4-methylphenol | 10.0 |
| Cupferron™ AL | 3.6 |

DPGDA is dipropylenediacrylate, available as Sartomer SR508 from ARKEMA.

Cupferron™ AL is aluminum N-nitrosophenylhydroxylamine from WAKO CHEMICALS LTD.

Dye-1 is a blue anthraquinone dye available as Macrolex™ Blue 3R from LANXESS.

Phenol-1 is a phenolic monomer prepared as disclosed in US20100249276 (Designer Molecules Inc.).

Phenol-3 is a phenolic monomer prepared according to the following scheme:

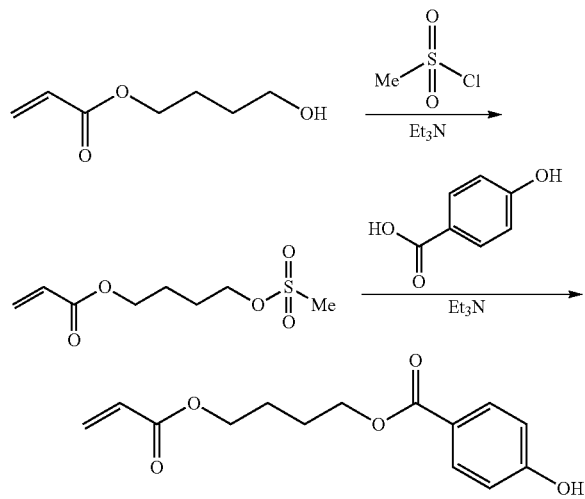

The mesylation step was disclosed JP2009221124 (Fujifilm Corporation).

Phenol-3 was prepared according to US2016/0318845 (Fujifilm Corporation).

Disperbyk 162 is a dispersing agent and has been precipitated from a solution available from BYK (ALTANA).

Cyan is SUN FAST BLUE 15:4, a cyan pigment available from SUN CHEMICALS.

Yellow is CROMOPHTAL YELLOW D 1085J, a yellow pigment from BASF.CTFA

VEEA is 2-(vinylethoxy)ethyl acrylate available from NIPPON SHOKUBAI, Japan.

CD420 is a monofunctional acrylic monomer available as Sartomer™ CD420 from ARKEMA.

TMPTA is trimethylol propane triacrylate, available as Sartomer™ SR351 from ARKEMA.

SR335 is a laurylacrylate from ARKEMA

ADK FP600 is a flame retardant from ADEKA PALMAROLE.

PB5 is a branched poly(4-hydroxystyrene) from HYDRITE CHEMICAL COMPANY.

BAPO is a bis(2,4,6-trimethylbenzoyl)-phenylphoshineoxide photoinitiator available as Irgacure™ 819 from BASF.

Ebecryl 1360 AK is a polysiloxane hexa acrylate slip agent from ALLNEX.

Methods

Viscosity

The viscosity of the inks was measured at 45° C. and at a shear rate of 1000 $s^{-1}$ using a "Robotic Viscometer Type VISCObot" from CAMBRIDGE APPLIED SYSTEMS.

For industrial inkjet printing, the viscosity at 45° C. and at a shear rate of 1000 $s^{-1}$ is preferably between 5.0 and 15 mPa·s. More preferably the viscosity at 45° C. and at a shear rate of 1000 $s^{-1}$ is less than 15 mPa·s.

Copper Cleaning

Isola™ 400 copper plates from Isola were cleaned for 5 seconds at 25° C. with a solution called Mecbrite™ CA-95 from MEC Europe, which has pH<1 and contained $H_2SO_4$, $H_2O_2$ and $Cu^{2+}$. During this operation a thin top layer of Cu (0.3-0.5 μm) was removed. The plates were then rinsed with a water jet for 90 seconds, dried and used immediately.

Etch Resistance

In a first method, the etch resistance was evaluated by rubbing a cotton bud over the layer immediately after etching and rinsing. Evaluation was made in accordance with a criteria described in Table 4.

TABLE 4

| Evaluation | Criterion |
|---|---|
| OK | Layer not damaged |
| NOK | Layer damaged |

In a second method, the etch resistance was evaluated by determining the percentage of the cured inkjet ink layer that remained on the copper plate after etching and rinsing. An etch resistance of 100% means that that the whole cured inkjet layer survived the etching bath. An etch resistance of 0% means that no cured inkjet ink could be found to be present on the copper plate after etching. A good etch resistance means a value of at least 80% Excellent etch resistance means a value of at least 90% but preferably 100%.

Strippability

The strippability was evaluated by determining the percentage of the cured inkjet layer that was removed from the copper plate after stripping. A strippability of 100% means that the whole cured inkjet ink layer was removed from the copper plate. An intermediate percentage, e.g. 30%, means that only 30% of the cured inkjet ink could be removed from the copper plate. A good strippability means a value of at least 80%. Excellent strippability means a value of at least 90% but preferably 100%. A value of 30% or less is a very poor strippability.

Adhesion of Solder Mask Inkjet Inks

The adhesion was evaluated by a cross-cut test according to ISO2409:1992(E). Paints (International standard 1992-08-15) using a Braive No. 1536 Cross Cut Tester from BRAIVE INSTRUMENTS with spacing of a 1 mm between cuts and using a weight of 600 g, in combination with a Tesatape™ 4104 PVC tape. The evaluation was made in accordance with a criterion described in Table 5, where both the adhesion in the cross-cut and outside the cross-cut were evaluated.

TABLE 5

| Evaluation value | Criterion |
| --- | --- |
| 0 | Nothing removed, perfect adhesion. |
| 1 | Detachment of only very small parts of the cured layer, almost perfect adhesion. |
| 2 | Minor parts of the cured layer was removed by the tape, good adhesion |
| 3 | Parts of the cured layer were removed by the tape, poor adhesion. |
| 4 | Most of the cured layer was removed by the tape, poor adhesion. |
| 5 | The cured layer was completely removed from the substrate by the tape, no adhesion. |

Solder Resistance

The solder resistance of the solder mask inkjet inks was evaluated using a SPL600240 Digital Dynamic Solder Pot available from L&M PRODUCTS filled with a "K" Grade 63:37 tin/lead solder available from SOLDER CONNECTION. The temperature of the solder was set at 290° C.

Using a Q-tip, a solder flux SC7560A from SOLDER CONNECTION was applied on the surface of the samples (i.e. coatings of the solder mask inkjet ink on a copper surface as described under adhesion) to clean the surface. The solder flux was dried by placing the samples for 10 minutes above the solder pot.

After placing the sample in the solder pot, a solder wave was created for 10 seconds after which the samples were cooled for at least 10 minutes.

The adhesion of the solder mask inkjet inks on the copper surface was then evaluated with a tape test on the cooled samples. A black tape Tesa 4104/04 from TESA AG, Germany was taped onto the coating and the tape was removed immediately thereafter by hand.

A visual evaluation resulted in an adhesion quality ranging from 0 (very good adhesion) to 5 (very poor adhesion).

Example 1

This example illustrates the preparation of adhesion promoters according to the present invention.

Synthesis of THIO-1

THIO-1 is a thioether adhesion promotor prepared according to the following scheme:

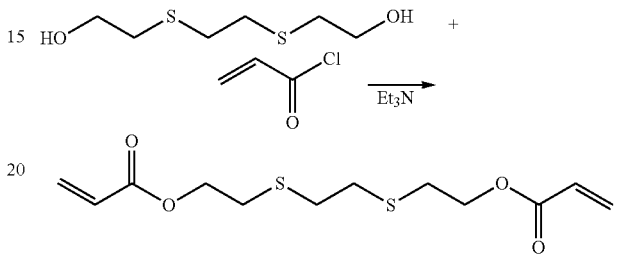

36.46 g (0.2 mol) 3,6-dithiaoctan-1,8-diol and 2.2 g BHT (butylhydroxytoluene) were dissolved in 350 ml methylene chloride. 44.44 g (0.44 mol) triethyl amine was added and the mixture was cooled to −5° C.

A solution of 39.82 g (0.44 mol) acryloyl chloride in 50 ml methylene chloride was added over 45 minutes while keeping the temperature at −5° C. The reaction was allowed to continue for two hours at room temperature. The mixture was extracted twice with 2 N HCl and twice with 2 N NaOH.

The organic fraction was isolated, dried over $Na_2SO_4$ and evaporated under reduced pressure.

The crude THIO-1 was purified by preparative column chromatography on a GraceResolv column using methylene chloride as eluent.

24 g (yield=41%) of THIO-1 was isolated (TLC-analysis on a Merck TLC Silica gel 60F254 plate, using methylene chloride as eluent: Rf=0.35).

Synthesis of THIO-2

THIO-2 is a thioether adhesion promotor supplied by ABCR.

Synthesis of THIO-7

THIO-7 is a thioether adhesion promotor prepared according to the following scheme:

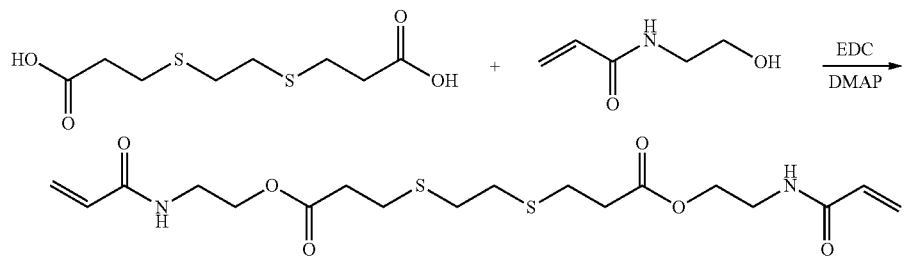

4,7-dithiadecanedioic acid was prepared according to Yoda N., Makromoleculare Chemie, 56, 36-54 (1962).

5.66 g (23.75 mmol) 4,7-dithiadecanedioic acid, 8.84 g (57 mmol) 1-(3-dimethylaminopropyl)-3-ethylcarbodiimide and 0.58 g (4.75 mmol) 4-dimethylaminopyridine were dissolved in 115 ml dimethylformamide. The mixture was cooled to −5° C. and a solution of 6.56 g (57 mmol) 2-hydroxyethylacrylamide in 10 ml dimethylformamide was added. The reaction was allowed to continue at room temperature for 16 hours. The solvent was removed under reduced pressure. The residue was redissolved 250 ml methylene chloride. The mixture was extracted three times with 75 ml water, once with 50 ml 1M HCl and once with 1M NaOH. The organic fraction was isolated, dried over $Na_2SO_4$ and evaporated under reduced pressure. The residue was treated with a mixture of 30 ml acetone and 30 ml methylene chloride. 300 ml n.hexane was added and THIO-7 crystallized from the medium. THIO-7 was isolated by filtration and dried. 3.4 g THIO-7 was isolated (yield=33%) THIO-7 was analyzed by $^1$H-NMR analysis in DMSO d6.

Comparative Sample COMP-S-1 and Inventive Sample INV-S-1

The comparative sample COMP-S-1 and the inventive test sample INV-S-1 were obtained by respectively coating the inks COMP-1 and INV-1 on a 35 µm copper laminate with a spiral coating bar of 20 µm wet coating thickness. Subsequently the layer was cured with a H-bulb (mercury lamp) at full power.

The samples were subjected to an etch bath (Metex Universal Starter from MacDermid Enthone containing $CuNH_3Cl$) for 60 seconds at 45° C. and then subsequently rinsed for 90 seconds with water and dried.

The etch resistance of the samples was evaluated as described above. The results are shown in Table 7.

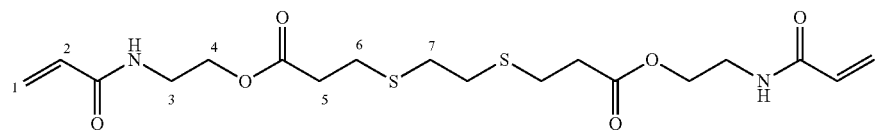 [SMILES: C=CC(=O)NCCOC(=O)CCSCCSCCC(=O)OCCNC(=O)C=C]

| Proton | Chemical shift (integration) |
|---|---|
| 1 | 6.09 (2H), 5.6 (2H) |
| 2 | 6.21 (2H) |
| 3 | 3.37 (4H) |
| 4 | 4.08 (4H) |
| 5 | 2.73 (4H) |
| 6 | 2.58 (4H) |
| 7 | 2.7 (4H) |

Example 2

This example illustrates the superior etch resistance combined with a good strippability in an alkaline stripping bath of UV curable inkjet inks including adhesion promoters according to the present invention.

Comparative Inks COMP-1 and Inventive Ink INV-1

The comparative radiation curable inkjet inks COMP-1 and the inventive radiation curable inkjet ink INV-1 were prepared according to Table 6. The weight percentages (wt %) are all based on the total weight of the radiation curable inkjet ink.

TABLE 6

| wt % of component | COMP-1 | INV-1 |
|---|---|---|
| SR606 | 46.55 | 42.55 |
| ACMO | 40.50 | 37.50 |
| THIO-1 | — | 7.00 |
| INHIB | 1.00 | 1.00 |
| ITX | 4.00 | 4.00 |
| TPO-L | 3.00 | 3.00 |
| EPD | 4.00 | 4.00 |
| DYE-1 | 1 | 1 |

The samples were than stripped in a 10% ethanolamine solution at 50° C. during 2 minutes. The strippability was evaluated as described above, the results are also shown in Table 7.

TABLE 7

| Etch resist sample | Etching Resistance | % ink after etching | Strippability |
|---|---|---|---|
| COMP-S-1 | NOK | 80% | OK |
| INV-S-1 | OK | 90% | OK |

From the results of Table 7 can be concluded that only the UV curable etch resist ink according to the present invention, i.e. containing an adhesion promoting compound as described above, combines an excellent etch resistance and a good strippability in an alkaline stripping bath.

Example 3

This example illustrates the superior etch resistance combined with a good strippability in an alkaline stripping bath of UV curable inkjet inks including adhesion promoters according to the present invention.

Comparative Inks COMP-2 to COMP-5 and Inventive Inks INV-2 and INV-3

The comparative radiation curable inkjet inks COMP-2 to COMP-5 and the inventive radiation curable inkjet inks INV-2 and 3 were prepared according to Table 8. The weight percentages (wt %) are all based on the total weight of the radiation curable inkjet ink.

TABLE 8

| wt % of component | COMP-2 | COMP-3 | COMP-4 | COMP-5 | INV-2 | INV-3 |
|---|---|---|---|---|---|---|
| SR606 | 42.50 | 44.00 | 44.50 | 46.50 | 42.50 | 43.50 |
| ACMO | 37.50 | 39.00 | 39.50 | 40.50 | 37.50 | 38.50 |

TABLE 8-continued

| wt % of component | COMP-2 | COMP-3 | COMP-4 | COMP-5 | INV-2 | INV-3 |
|---|---|---|---|---|---|---|
| Phenol-1 | — | 4.00 | — | — | 4.00 | 4.00 |
| CEA | 3.00 | | | | | |
| CN146 | 4.00 | — | — | — | — | — |
| THIO-2 | — | — | 3.00 | — | 3.00 | 1.00 |
| INHIB | 1.00 | = | = | = | = | — |
| ITX | 4.00 | = | = | = | = | = |
| TPO-L | 3.00 | = | = | = | = | = |
| EPD | 4.00 | = | = | = | = | = |
| DYE-1 | 1 | = | = | = | = | = |

Samples COMP-S-2 to COMP-S-5 and Inventive Test Samples INV-S-2 and INV-S-3

The comparative samples COMP-S-2 to COMP-S-5 and the inventive test samples INV-S-2 and INV-S-3 were obtained by jetting the inks COMP-2 to COMP-5 and INV-1 and INV-2 on a 35 μm Cu laminate using a Microcraft MJK2013 (8 pass, 45° C. jetting temperature, 100% pincure after each pass with a LED 395 nm bulb at full power).

The samples were subjected to an etch bath (Metex Universal Starter from MacDermid Enthone containing $CuNH_3Cl$) for 60 seconds at 45° C. and then subsequently rinsed for 90 seconds with water and dried.

The etch resistance of the samples was evaluated as described above. The results are shown in Table 9.

The samples were than stripped in a 6.25% NaOH solution at 50° C. during 2 minutes. The strippability was evaluated as described above, the results are also shown in Table 9.

TABLE 9

| Etch resist sample | Etching Resistance | Rinsing resistance | % ink after etching | Strippability |
|---|---|---|---|---|
| COMP-S-2 | NOK | NOK | 40% | OK |
| COMP-S-3 | NOK | NOK | 50% | OK |
| COMP-S-4 | NOK | NOK | 50% | OK |
| COMP-S-5 | NOK | NOK | 70% | OK |
| INV-S-2 | OK | OK | 100% | OK |
| INV-S-3 | OK | NOK | 95% | OK |

From the results of Table 9 can be concluded that only the UV curable etch resist ink according to the present invention combine an excellent etch resistance and a good strippability in an alkaline stripping bath.

Example 4

This example illustrates that an UV curable inkjet ink according to the present invention may also be used as a solder mask inkjet ink combining a good adhesion towards copper and a good solder resistance.

Cyan and Yellow Pigment Dispersions CPD and YPD

Concentrated Cyan and Yellow and pigment dispersions, respectively CPD and YPD, were prepared having a composition according to Table 10.

TABLE 10

| wt % of: | CPD | YPD |
|---|---|---|
| Cyan | 15 | — |
| Yellow | — | 15 |
| Disperbyk 162 | 15 | = |
| INHIB | 1 | = |
| VEEA | 69 | = |

CPD and YPD were prepared as follows: 138 g of 2-(2-vinyloxyethoxy)ethyl acrylate, 2 g of a solution containing 4 wt % of 4-methoxyphenol, 10 wt % of 2,6-Di-tert-butyl-4-methylphenol and 3.6 wt % of Aluminum-N-nitroso phenylhydroxyl amine in dipropylene glycol diacrylate, 200 g of a 30 wt % solution of Disperbyk 162 in 2-(2-Vinyloxyethoxy)ethyl acrylate and 60 g of Cyan (for CPD) or 60 g of Yellow (for YPD) were mixed using a DISPERLUX™ dispenser. Stirring was continued for 30 minutes. The vessel was connected to a NETZSCH MiniZeta mill filled with 900 g of 0.4 mm yttrium stabilized zirconia beads ("high wear resistant zirconia grinding media" from TOSOH Co.). The mixture was circulated over the mill for 120 minutes (residence time of 45 minutes) and a rotation speed in the mill of about 10.4 m/s. During the complete milling procedure the content in the mill was cooled to keep the temperature below 60° C. After milling, the dispersion was discharged into a vessel.

The resulting concentrated pigment dispersions CPD and YPD exhibited an average particle size of respectively 80 nm and 131 nm, as measured with a Malvern™ nano-S, and a viscosity of respectively 51 mPa·s and 114 mPa·s at 25° C. and at a shear rate of 10 $s^{-1}$.

Preparation of Comparative Ink COMP-6 and Inventive Inks INV-4 to INV-5

The comparative radiation curable inkjet ink COMP-6 and the inventive radiation curable inkjet ink INV-4 to INV-5 were prepared according to Table 11. The weight percentages (wt %) are all based on the total weight of the radiation curable inkjet ink.

TABLE 11

| wt % of component | COMP-6 | INV-4 | INV-5 |
|---|---|---|---|
| CPD | 3.30 | = | = |
| YPD | 3.30 | = | = |
| CTFA | 20.00 | = | = |
| VEEA | 25.40 | 24.40 | = |
| ACMO | 5.00 | = | = |
| CD420 | 15.00 | = | = |
| TMPTA | 5.00 | = | = |
| SR335 | 5.00 | = | = |
| ADK FP600 | 2.00 | = | = |
| PB5 | 5.00 | = | = |
| ITX | 4.00 | = | = |
| EPD | 4.00 | = | = |
| BAPO | 2.00 | = | = |
| THIO-01 | — | 1.00 | — |
| THIO-02 | — | — | 1.00 |
| Ebecryl 1360 AK | 0.10 | = | = |
| INHIB | 0.90 | = | = |

The comparative sample COMP-6 and the inventive samples INV-4 to INV-05 were obtained by jetting the inks on a 35 μm brushed Cu laminate using a Microcraft MJK2013 (8 pass, 45° C. jetting temperature, 15% pincure after each pass using a LED 395 nm lamp). Additionally a thermal cure at 150° C. during 60 minutes was performed.

The solder resistance of the Comparative ink COMP-06 and the inventive inks INV-04 to INV-05 were tested as described above. The results are shown in Table 12.

TABLE 12

| UV curable ink jet ink | Adhesion | Solder Resistance |
|---|---|---|
| COMP-6 | 3 | 0 |
| INV-4 | 1 | 0 |
| INV-5 | 0 | 0 |

It is clear from the results of Table 12 that the inventive solder mask inkjet inks containing an adhesion promoter according to the present invention all have an improved adhesion towards the Cu-surface and a superior solder resistance compared to a solder mask inkjet ink without such an adhesion promoter.

The invention claimed is:

1. A method of manufacturing a Printed Circuit Board (PCB) wherein an inkjet printing step is used, characterized in that in the inkjet printing step a radiation curable inkjet ink comprising an adhesion promoter having a chemical structure according to Formula II is image-wise jetted and cured on a substrate, Formula II

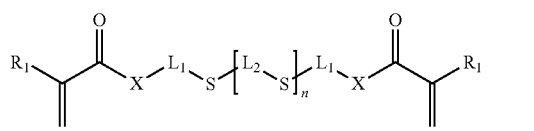

wherein

X is selected from the group consisting of O and $NR_3$, $L_1$ and $L_2$ independently represent a divalent linking group comprising from 2 to 20 carbon atoms, each $R_1$ is independently selected from the group consisting of hydrogen, a substituted or unsubstituted alkyl group and a substituted or unsubstituted aryl group, $R_3$ is selected from the group consisting of hydrogen, a substituted or unsubstituted alkyl group, a substituted or unsubstituted alkenyl group, a substituted or unsubstituted alkynyl group, a substituted or unsubstituted alkaryl group, a substituted or unsubstituted aralkyl group and a substituted or unsubstituted (hetero)aryl group, n represents an integer from 0 to 4, and any of $L_1$ and $L_2$ optionally represent the necessary atoms to form a 5 to 8 membered ring.

2. The method according to claim 1 wherein X is O.

3. The method according to claim 1 wherein $L_1$ and $L_2$ independently represent a substituted or unsubstituted alkylene group.

4. The method according to claim 1 wherein n is 1.

5. The method according to claim 1 wherein curing is carried out using UV radiation.

6. The method according to claim 1 wherein a solder mask is provided on a dielectric substrate containing an electrically conductive pattern in the inkjet printing step.

7. The method according to claim 6 also comprising a heating step.

8. The method according to claim 1 wherein an etch resist is provided on a metal surface in the inkjet printing step.

9. The method according to claim 8 wherein the metal surface is a copper surface.

10. A radiation curable inkjet ink comprising a polymerizable compound having a pKa of at least 2.5 and an adhesion promoter having a chemical structure according to Formula II, Formula II

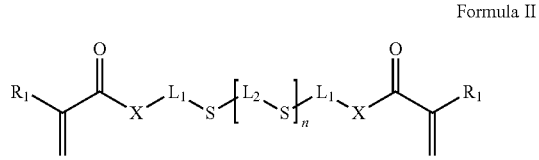

wherein

X is selected from the group consisting of O and $NR_3$, $L_1$ and $L_2$ independently represent a divalent linking group comprising from 2 to 20 carbon atoms, each $R_1$ is independently selected from the group consisting of hydrogen, a substituted or unsubstituted alkyl group and a substituted or unsubstituted aryl group, $R_3$ is selected from the group consisting of hydrogen, a substituted or unsubstituted alkyl group, a substituted or unsubstituted alkenyl group, a substituted or unsubstituted alkynyl group, a substituted or unsubstituted alkaryl group, a substituted or unsubstituted aralkyl group and a substituted or unsubstituted (hetero)aryl group, n represents an integer from 0 to 4, and any of $L_1$ and $L_2$ optionally represent the necessary atoms to form a 5 to 8 membered ring.

11. The method according to claim 8 wherein a radiation curable inkjet ink comprising a polymerizable compound having a pKa of at least 2.5 is used.

12. The radiation curable inkjet ink according to claim 10 wherein the polymerizable compound is a phenolic monomer.

13. The radiation curable inkjet ink according to claim 12 wherein the phenolic monomer is selected from the group consisting of a phenolic acrylate, a phenolic methacrylate, a phenolic acrylamide and a phenolic methacrylamide.

* * * * *